(12) United States Patent
Danz et al.

(10) Patent No.: US 7,236,855 B2
(45) Date of Patent: Jun. 26, 2007

(54) METHOD FOR COMPENSATING AND OUT-OF-BALANCE CONDITION OF A ROTATING BODY

(75) Inventors: Günter Danz, Gross-Zimmern (DE); Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 179 days.

(21) Appl. No.: 11/045,892

(22) Filed: Jan. 28, 2005

(65) Prior Publication Data

US 2005/0192709 A1    Sep. 1, 2005

(30) Foreign Application Priority Data

Jan. 28, 2004   (DE)   .............. 10 2004 004 298

(51) Int. Cl.
*G01M 1/38* (2006.01)

(52) U.S. Cl. ........................................ 700/279; 73/458

(58) Field of Classification Search .............. 73/1.82, 73/1.84, 65.01, 66, 457, 458, 460–462, 468–470; 700/279, 280; 378/4, 21
See application file for complete search history.

(56) References Cited

U.S. PATENT DOCUMENTS

| | | | |
|---|---|---|---|
| 5,109,397 A * | 4/1992 | Gordon et al. | 378/205 |
| 5,201,586 A | 4/1993 | Zimmermann et al. | |
| 5,448,608 A * | 9/1995 | Swain et al. | 378/4 |
| 5,627,762 A * | 5/1997 | Cameron et al. | 700/279 |
| 6,189,372 B1 | 2/2001 | Danz | |
| 6,210,099 B1 | 4/2001 | Hugbart et al. | |
| 6,250,155 B1 | 6/2001 | Hormann et al. | |
| 6,354,151 B1 | 3/2002 | Freyermuth et al. | |
| 6,412,345 B1 * | 7/2002 | Murray et al. | 73/468 |
| 6,550,317 B2 * | 4/2003 | Steinlage et al. | 73/65.01 |
| 6,590,960 B2 | 7/2003 | Kroener et al. | |
| 6,606,922 B2 * | 8/2003 | Case et al. | 464/180 |
| 6,748,806 B2 * | 6/2004 | Halsmer | 73/462 |
| 2003/0159508 A1 | 8/2003 | Halsmer | |
| 2005/0119847 A1 * | 6/2005 | Park | 702/105 |

FOREIGN PATENT DOCUMENTS

| | | |
|---|---|---|
| DE | 28 52 376 | 7/1980 |
| DE | 32 48 085 | 7/1986 |
| DE | 297 09 273 | 9/1997 |
| DE | 197 29 172 | 7/1998 |
| DE | 197 43 577 | 4/1999 |
| DE | 299 13 630 | 4/2000 |
| DE | 199 20 698 | 12/2000 |
| DE | 199 20 699 | 10/2001 |
| WO | WO 2004/098413 | 11/2004 |

* cited by examiner

OTHER PUBLICATIONS

Abstracts of Japan Application 2001276045.

*Primary Examiner*—Maria N. Von Buhr
(74) *Attorney, Agent, or Firm*—Schiff Hardin LLP

(57) ABSTRACT

In a method for compensation of an out-of-balance condition of an imaging data acquisition device, rotatable around a patient opening of a stationary unit of a tomography apparatus, such as an x-ray computed tomography apparatus or an ultrasound tomography apparatus, the data acquisition device being rotatably mounted such that it can rotate around an axis in a bearing of the stationary unit, vibrations transferred to the stationary unit by the out-of-balance condition of the data acquisition device, at least one of the out-of-balance vectors causing the out-of-balance condition is determined from the vibration measurement, and the axis of the data acquisition device is adjusted with regard to an axis of the bearing to compensate the out-of-balance condition.

11 Claims, 2 Drawing Sheets

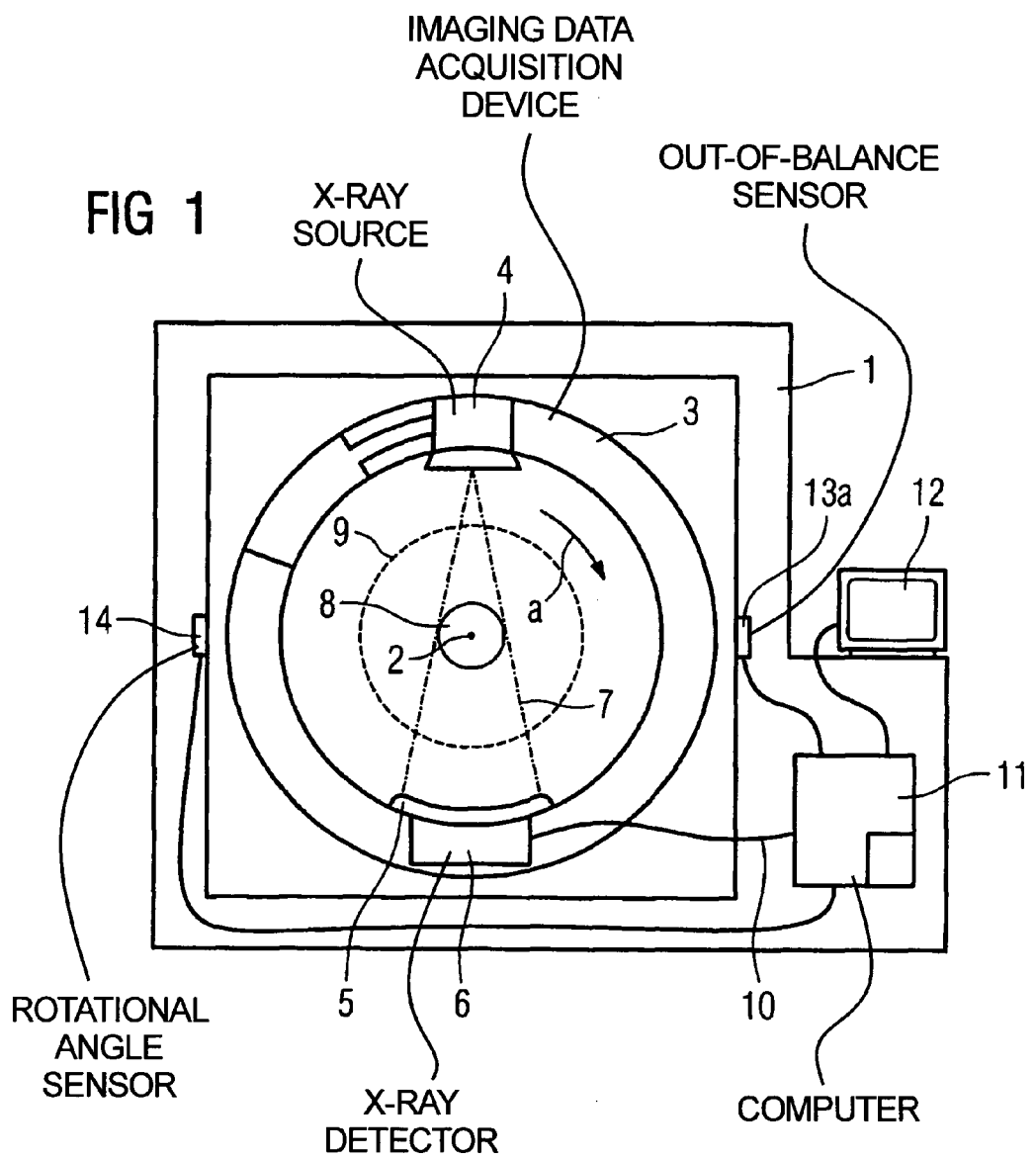

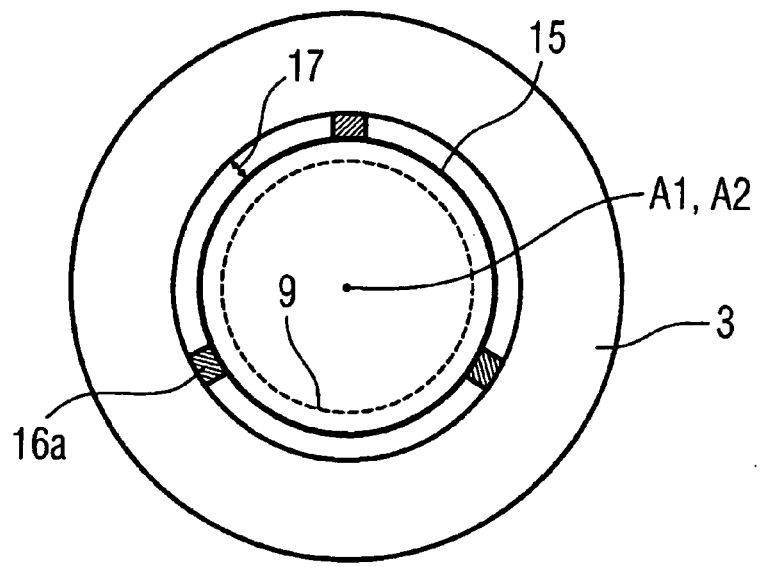
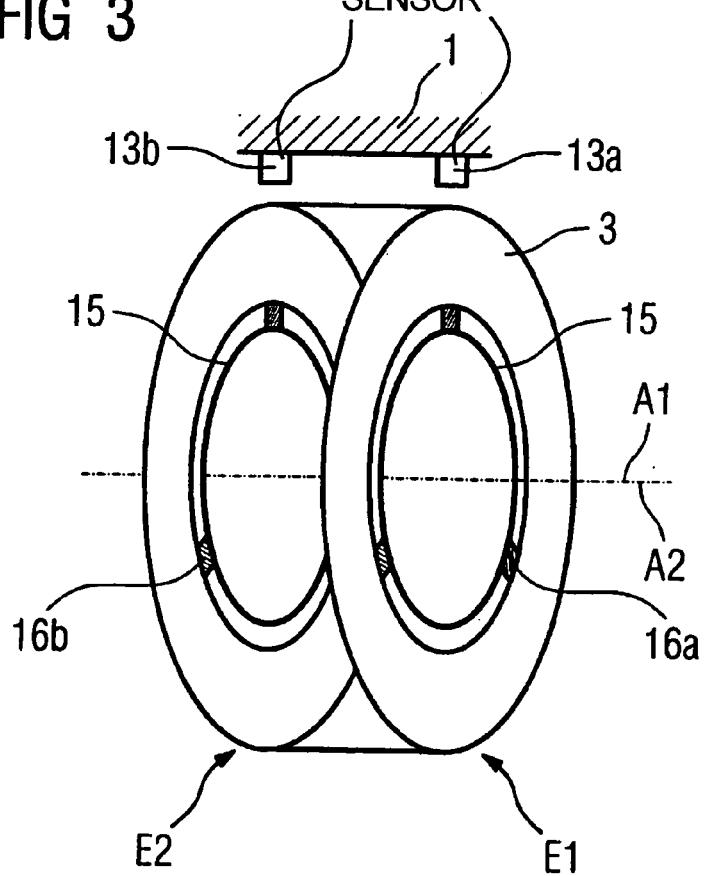

US 7,236,855 B2

METHOD FOR COMPENSATING AND OUT-OF-BALANCE CONDITION OF A ROTATING BODY

BACKGROUND OF THE INVENTION

1. Field of the Invention

The invention concerns a method for compensation of the out-of-balance condition of a rotating body, such as a data acquisition device of a tomography apparatus.

2. Description of the Prior Art

An x-ray computed tomography apparatus is known from German OS 101 08 065. A data acquisition device or gantry, mounted such that it can be rotated around a horizontal rotational axis, is accommodated in a stationary mount. A sensor to detect an out-of-balance (unbalanced) condition of the data acquisition device is provided on the stationary mount. The sensor is connected with a device to calculate the position or positions of the rotatable data acquisition device at which a compensation weight or weights should be applied to compensate the out-of-balance condition. The balancing can ensue without the use of a specific balancing device, but a trained person is required to implement the balancing procedure, in particular for correct application of the compensation weights. The balancing procedure requires, among other things, a partial demounting of parts of the x-ray computed tomography apparatus. This procedure thus is time-consuming and expensive.

U.S. Pat. No. 6,354,151 as well as German Translation 698 04 817 T2 describe an apparatus for balancing of an instrument mounting. The mass of the instrument mounting and its out-of-balance condition are thereby determined.

German Utility Model 297 09 273 discloses a balancing device for balancing rotors. Two compensation rings with a defined out-of-balance condition are provided that can be attached to one another on the rotor at suitable relative positions for compensation of an out-of-balance condition of the rotor.

German PS 199 20 699 also discloses a method for balancing rotors. Two compensation rings respectively exhibiting a defined out-of-balance condition are mounted on the rotor. To compensate the out-of-balance condition, the relative positions of the compensation rings relative to one another can be changed. For this purpose, an attachment device of the compensation rings is released. The compensation rings are held by a pawl and the rotor is rotated by a predetermined angle relative to the compensation rings. The compensation rings are subsequently locked (arrested).

To ease the locking of such compensation rings, in German OS 199 20 698 it is disclosed to fix the rings in their relative positions by means of a spring-loaded locking device on the rotor. By means of an applied force, the compensation rings can be displaced in their relative positions relative to the rotor and naturally can be locked.

To ease the identification of the correct locking position of such compensation rings, in German Utility Model 298 23 562 discloses projecting markings onto the compensation elements by means of a marking device when the rotor is located in a compensation position.

German PS 197 29 172 discloses a method for continuous compensation of an out-of-balance rotor. The out-of-balance condition of the rotor is measured by means of an out-of-balance measurement device. For compensation of the out-of-balance condition, the rotor has a number of compensation chambers filled with compensation fluid and disposed at different relative rotor positions. To compensate the out-of-balance condition, the quantity of the compensation fluid in the compensation chambers is increased or reduced in a suitable manner.

German Utility Model 299 13 630 concerns an apparatus for compensation of an out-of-balance condition in a machine tool or balancing machine. The balancing machine is thereby balanced using counterweight rotors and the position of the counterweight rotors is stored. The balancing machine is subsequently re-balanced with a component incorporated therein by displacement of the counterweight rotors. The out-of-balance condition of the component can be inferred from the deviating position of the counterweight rotors without and with the component.

German OS 197 43 577 and German OS 197 43 578 disclose a method for balancing a rotating body. Compensation masses that can be radially displaced and/or displaced in terms of their relative positions with respect to the rotating body are attached to the rotating body. At the beginning of the method, the compensation masses are initially brought into a zero position in which the vectors generated by them mutually cancel. The out-of-balance condition of the rotating body is subsequently measured and compensated by suitable shifting of the compensation masses.

The implementation of the methods known according to the prior art typically requires technically trained personnel. Independent of this, some of the known methods are not suited for balancing of a measurement device of tomography apparatuses.

SUMMARY OF THE INVENTION

An object of the invention to remedy the aforementioned disadvantages according to the prior art. In particular, a method for compensation of the out-of-balance condition of a measurement device should be provided which can be fully automatically and simply implemented.

This object is achieved according to the invention by a method for compensation of the out-of-balance condition of an image data acquisition device, rotatable around a patient opening of a tomography apparatus (in particular an x-ray computed tomography apparatus or an ultrasound tomography apparatus) which is mounted such that it can rotate around an axis in a bearing of a stationary unit, including the steps of measurement of the vibrations transferred to the stationary unit by the out-of-balance condition of the data acquisition device, determination of at least one of the out-of-balance vectors causing the out-of-balance condition, and the axis of the measurement device is adjusted with regard to an axis of the bearing to compensate the out-of-balance vector.

In practice, an out-of-balance condition is normally caused by a number of out-of-balance vectors. According to the inventive method, the axis of the measurement device is adjusted with regard to the axis of the bearing such that all out-of-balance vectors are compensated.

In an embodiment of the invention, a device is provided to adjust the axis of the measurement device with regard to the axis of the bearing. This enables a wholly automatic balancing of the data acquisition device. For this purpose, it is not necessary to provide separate compensation weights on the measurement device. The tomography apparatus thus can be realized with relatively little outlay.

As used herein, the "axis" of the data acquisition device means its geometrical axis or rotational axis. The rotational axis can in practice deviate from a center-of-gravity axis proceeding through the center of gravity of the measurement device. As a consequence of such a deviation, the measurement device exhibits an out-of-balance condition give rotation around the rotation axis. By an adjustment of the rotational axis of the data acquisition device with regard to the invariable axis of the bearing accommodating the data acquisition device, it can be achieved that tho center-of-gravity axis is brought into agreement with the axis of the bearing, and thus the out-of-balance condition of the data acquisition device is compensated.

In an embodiment, the device for adjustment has adjustment (displacement) elements that are arranged between the bearing and the data acquisition device in two parallel planes axially separated from one another. At least three uniform adjustment element disposed over the extent of the bearing are provided in each of the planes. The adjustment elements can in this case by offset by an angle of 120°. The adjustment elements can be operable electrically, magnetically, hydraulically or pneumatically. They can exhibit an adjustment path of at most 5 mm, preferably 1 mm. For example, to adjust the adjustment elements materials can be used that change their dimension in one direction upon application of a voltage or a magnetic field, For example, piezoelectric or magnetostrictive materials exhibit such properties. It has proven to be particularly advantageous to use a magnetostrictive adjustment elements.

Because the adjustment elements are disposed in two parallel planes axially separated from one another, it is possible to compensate radial out-of-balance vectors.

The out-of-balance condition can be detected by a sensor at the stationary unit that measures vibrations transferred to the stationary unit when the data acquisition device exhibits the out-of-balance condition.

According to a further embodiment, a further sensor is provided to determine the rotation angle of the data acquisition device with regard to the stationary unit. This enables a continuous determination of the rotation angle, and thus a simplified determination of the position of the out-of-balance condition of the data acquisition device. It is thus particularly simple to calculate the vectors opposite to the out-of-balance vectors.

The compensation of the out-of-balance condition can dynamically ensue during the rotation of the annular data acquisition device. For this purpose, a control device can be provided to control the adjustment elements according to a predetermined algorithm for compensation of the out-of-balance condition of the data acquisition device. The control device can be a conventional control device with a microprocessor, a computer or the like in which a suitable measurement, evaluation and control program are stored. The signals measured by the sensor and the further sensor can be evaluated and converted into corresponding adjustment signals for the adjustment arrangement for compensation of the out-of-balance condition. As a consequence of the adjustment signals, the adjustment elements change the position of the axis of the data acquisition device with regard to the axis of the bearing.

DESCRIPTION OF THE DRAWINGS

FIG. 1 is a schematic side view of an x-ray tomography apparatus.

FIG. 2 shows the apparatus according to FIG. 1 with adjustment elements.

FIG. 3 is a schematic view of the arrangement of the adjustment elements.

DESCRIPTION OF THE PREFERRED EMBODIMENTS

FIG. 1 schematically shows a side view of an x-ray tomography apparatus with a stationary unit 1. An annular imaging data acquisition device 3 (gantry) is accommodated on the stationary unit 1 such that it can rotate around a rotation axis 2 disposed at a right angle to the plane of the drawing. A rotational direction of the data acquisition device 3 is designated with the arrow a. An x-ray source 4 and an x-ray detector 5 with downstream evaluation electronic 6 are mounted on the data acquisition device 3 opposite to each other. A beam fan 7 radiated by the x-ray source 4 defines a circular measurement field 8 given a rotation of the data acquisition device 3. The measurement field 8 is located within a patient opening 9 indicated with the dashed line. In particular the evaluation electronics 6 are connected with a computer 11 via a slip ring contact 10 (indicated schematically), which computer 11 has a monitor 12 for display of data. First sensors for measurement of vibrations transferred to the stationary unit 1 are provided on the stationary unit 1. They are conventional sensors with which vibrations caused by an out-of-balance condition of the data acquisition device 3 and transferred to the stationary unit 1 can be measured in the radial direction and the axial direction. One such first sensor is designated with the reference character 13a in FIG. 1. A further sensor 14 attached to the stationary unit 1 serves for the detection of the rotation angle of the data acquisition device 3 relative to the stationary unit 1. The sensor 13a and the further sensor 14 are likewise connected with the computer 11 for evaluation of the signals measured therewith. In FIG. 1, for clarity compensation weights provided on the measurement device 3 are not shown.

FIG. 2 shows a schematic side view of the data acquisition device 3, wherein for clarity the x-ray source 4 and the x-ray detector 5 with the evaluation electronic 6 have been omitted. A bearing 15 accommodated on the stationary unit (not shown in FIG. 2) exhibits a first axis A1, perpendicular to the plane of the drawing that corresponds to the rotational axis 2 shown in FIG. 1. A geometric second axis A2 of the data acquisition device 3 here coincides with the first axis A1. The data acquisition device 3 is incorporated on the bearing 15 under interposition by first adjustment elements 16a disposed offset by 120°. The first adjustment elements 16a are arranged between an outer circumferential surface of the bearing 15 and the inner circumferential surface of the data acquisition device 3. A separation (designated with the arrow 16) between the outer circumference surface of the bearing 15 and the inner circumferential surface of the data acquisition device 3 can be changed by the first adjustment elements 16a. The adjustment elements can be, for example, a piezoelectric or magnetostrictive actuator with which a change of the separation 17 between the outer circumferential surface of the bearing 15 and the inner circumferential surface of the data acquisition device 3 by amounts of up to 1 mm can be realized.

As can be seen in FIG. 3, the first adjustment elements 16a can be mounted in a first plane E1 and three second adjustment elements 16b can be mounted in a parallel second plane E2 axially separated from the first. With the proposed arrangement, it is possible to also marginally adjust the second axis A2 at an angle to the first axis A1. Radial out-of-balance vectors thus can be compensated. First sensors 13a, 13b for measurement of the vibrations transferred to the stationary unit 1 are respectively associated with the first plane E1 and the second plane E2.

Compensation of an out-of-balance condition of a rotor, in particular the data acquisition device 3 of a tomography apparatus, can ensue according to the following.

The adjustment elements 16a, 16b are initially located in a starting (null) position in which the first axis A1 of the bearing 15 and the second axis A2 of the data acquisition device 3 are identical.

The data acquisition device 3 is rotated. The vibrations transferred to the stationary unit 1 by an out-of-balance condition of the first data acquisition device 3 are measured in the planes E1 and E2 by the first sensors 13a, 13b. The rotation angles of the data acquisition device 3 relative to the stationary unit 1 are simultaneously registered by the second sensor 14. Using a suitable calculation program stored in the computer 11, positions of the second axis A2 relative to the first axis A1 and suitable for compensation of the out-of-balance condition of the data acquisition device 3 are respectively calculated for both planes E1, E2. The result of the calculation is an angle and a separation of the first axis A1 from the second axis A2, respectively in the first plane E1 and in the second plane E2. According to the calculated distances and the associated angles, the first adjustment unit 16a as well as the second adjustment unit 16b are correspondingly activated such that the second axis A2 assumes a changed position relative to the first axis A1. The out-of-balance condition of the data acquisition device 3 is compensated in that its center-of-gravity axis is brought into agreement with the first axis A1 of the bearing 15.

The method can by implemented dynamically, i.e. during the rotation of a rotor or the data acquisition device 3. It is particularly effective in saving time. The method can be wholly automatically implemented. Trained personnel are not necessary for implementing the method.

Although modifications and changes may be suggested by those skilled in the art, it is the intention of the inventors to embody within the patent warranted hereon all changes and modifications as reasonably and properly come within the scope of their contribution to the art.

We claim:

1. A method for compensating an out-of-balance condition of an imaging data acquisition device mounted in a stationary unit for rotation around a bearing axis of a bearing in the stationary unit, said imaging data acquisition device having a device axis and said device axis and said bearing axis proceeding through a patient opening in the stationary unit, said method comprising the steps of:
   measuring vibrations transferred from the imaging data acquisition device to the stationary unit due to an out-of-balance condition of the imaging data acquisition device;
   dependent on the measured vibrations, determining at least one out-of-balance vector that contributes to the out-of-balance condition of the imaging data acquisition device; and
   physically adjusting said device axis with respect to said bearing axis to compensate said at least one out-of-balance vector, thereby compensating said out-of-balance condition of said imaging data acquisition device.

2. A method as claimed in claim 1 comprising adjusting said device axis with respect to said bearing axis in two parallel planes of said imaging data acquisition device that are axially separated from each other.

3. A method as claimed in claim 1 comprising adjusting said device axis with respect to said bearing axis by physically moving said imaging data acquisition device with an adjustment element disposed between said bearing and said imaging data acquisition device.

4. A method as claimed in claim 1 comprising uniformly distributing at least three adjustment elements around a circumference of said bearing, and physically moving said imaging data acquisition device by a combination of said adjustment elements.

5. A method as claimed in claim 4 comprising adjusting said device axis with respect to said bearing axis in two parallel planes in said imaging data acquisition device that are axially separated from each other, and uniformly distributing at least three adjustment elements around the circumference of the bearing in each of said planes.

6. A method as claimed in claim 3 comprising employing an adjustment element selected from the group consisting of magnetically operating adjustment elements, electrically operating adjustment elements, hydraulically operating adjustment elements and pneumatically operating adjustment elements.

7. A method as claimed in claim 3 comprising employing a magnetostrictive adjustment element as said adjustment element.

8. A method as claimed in claim 3 comprising adjusting said device axis relative to said bearing axis by adjusting said device axis through an adjustment path not exceeding 5 mm.

9. A method as claimed in claim 8 comprising adjusting said device axis relative to said bearing axis by adjusting said device axis through an adjustment path not exceeding 1 mm.

10. A method as claimed in claim 1 comprising measuring a rotational angle of said imaging data acquisition device relative to said stationary unit, and additionally employing said rotational angle to determine said at least one of said out-of-balance vectors.

11. A method as claimed in claim 1 comprising determining said at least one of said out-of-balance vectors in a control device according to a predetermined out-of-balance compensation algorithm, and automatically controlling said adjustment of said device axis with respect to said bearing axis with said control device.

* * * * *